(12) United States Patent
Wiemer et al.

(10) Patent No.: US 8,937,656 B2
(45) Date of Patent: Jan. 20, 2015

(54) METHOD AND INSPECTION DEVICE FOR TESTING CONTAINERS

(75) Inventors: Heinrich Wiemer, Hamburg (DE); Horst Böcker, Schwerte (DE); Jürgen Herrmann, Rosenheim (DE)

(73) Assignee: KHS GmbH, Dortmund (DE)

( * ) Notice: Subject to any disclaimer, the term of this patent is extended or adjusted under 35 U.S.C. 154(b) by 985 days.

(21) Appl. No.: 13/063,475

(22) PCT Filed: Nov. 27, 2009

(86) PCT No.: PCT/EP2009/008462
§ 371 (c)(1),
(2), (4) Date: Mar. 11, 2011

(87) PCT Pub. No.: WO2010/075918
PCT Pub. Date: Jul. 8, 2010

(65) Prior Publication Data
US 2011/0164131 A1    Jul. 7, 2011

(30) Foreign Application Priority Data
Dec. 17, 2008 (DE) .......................... 10 2008 062 385

(51) Int. Cl.
*H04N 7/18* (2006.01)
*B67B 3/26* (2006.01)
*G01N 21/90* (2006.01)

(52) U.S. Cl.
CPC ............... *B67B 3/262* (2013.01); *G01N 21/90* (2013.01)
USPC .......................................... 348/127; 348/145

(58) Field of Classification Search
USPC ......... 348/127, 125, 131, 135, 137, 139, 142; 386/227, 223
See application file for complete search history.

(56) References Cited

U.S. PATENT DOCUMENTS

| 4,746,212 A | 5/1988 | Sudo et al. |
| 6,104,482 A | 8/2000 | Brower et al. |
| 7,574,845 B2 | 8/2009 | Varhaniovsky |

FOREIGN PATENT DOCUMENTS

| CN | 1299050 A | 6/2001 |
| CN | 101046480 A | 10/2007 |
| CN | 101149349 A | 3/2008 |
| DE | 3610416 | 10/1986 |
| DE | 10140009 | 3/2003 |
| EP | 0062935 | 10/1982 |
| EP | 0708325 | 4/1996 |
| EP | 1270433 | 1/2003 |
| EP | 1293473 | 3/2003 |
| GB | 2135447 | 8/1984 |
| GB | 2173299 | 10/1986 |
| JP | 2006-300711 | 11/2006 |
| WO | 03/016886 | 2/2003 |
| WO | 2004/113221 | 12/2004 |

*Primary Examiner* — Robert Chevalier
(74) *Attorney, Agent, or Firm* — Occhiuti & Rohlicek LLP

(57) ABSTRACT

The invention relates to a method for testing bottles or the like containers (1) filled with a bulk material and mechanically closed by means of a container closure (2), the container closures (2) each comprising an original security ring (4) held on said container (1) in the closed state thereof in an interlocking and/or force-fit manner, such that opening the container (1) is possible only by separating and/or destroying the originality security ring (4), characterized in that the containers (1) are tested by means of at least one optoelectronic sensor system (10) after filling and closing for intactness of the originality security element (4).

23 Claims, 4 Drawing Sheets

METHOD AND INSPECTION DEVICE FOR TESTING CONTAINERS

RELATED APPLICATIONS

This application is the national stage entry, under 35 USC 371, of PCT application PCT/EP2009/008462, filed on Nov. 27, 2009, which claims the benefit of the Dec. 17, 2008 priority date of DE 10 2008 062 385.7, the contents of which are herein incorporated by reference.

FIELD OF INVENTION

The invention relates to testing containers, and in particular, to testing containers closed by a security element.

BACKGROUND

It is a common and well-known practice to close a filled container at its container opening with a container closure that is simultaneously also provided with a security element. This assures the quality and originality of the product and is therefore referred to henceforth as either the "originality-security element" or the "tamper-evident band."

When a container is closed mechanically, the originality-security element interlocks on the container so that it is only possible to open the container and/or the container closure by detaching the originality-security element from the closure and/or destroying the element. As a result, the opening of the container is indicated with relative certainty.

In the case of a container closure that can be processed mechanically, in particular in the case of cap-type closures for bottles or similar containers, the originality-security element usually comprises a quality or originality-security ring that is provided, for example, on the open side of the cap-type container closure or of the closure body. On application of the container closure to a container, for example when the container closure in the form of a screw closure is screwed on, the security ring engages from behind in the area of the container's opening and/or on its neck in an interlocking manner.

In the case of screw closures for mechanical closure of containers, it is known to produce the originality-security ring and the closure body of the container closure in a single piece and to provide at least one ring-shaped predetermined break-line between the originality-security ring and the closure body. It is also known to design the originality-security ring in such a way that it consists of several ring segments that are connected to each other by pre-determined breaking sections separated by predetermined break-lines. The predetermined break-lines and sections are, for example, formed by reducing the material thickness and/or by perforation. As a result, opening the container closure not only detaches the originality-security ring from the closure cap, but also damages it.

Since originality-security elements are thus constructively designed such that they are destroyed when stressed, it is difficult to completely prevent security elements from sometimes being damaged during the mechanical closure of containers. This leads to irritation and complaints both from retailers in the trade and from consumers. It also leads to increased costs. Damage of this kind to the originality-security elements is thus undesirable.

SUMMARY

The invention provides a method for identifying damaged originality-security elements, or tamper-evident bands, on containers. This reduces irritations and complaints due to damaged originality-security elements or tamper-evident bands on containers.

In one aspect, the invention features a method for checking filled containers that have been sealed with container seals. Such a method includes checking integrity of a tamper-evident band provided on a container seal that is retained on a container in at least one of a form locking manner and a force locking manner when the container is sealed, wherein the container can only be opened by at least one of removal and destruction of the tamper-evident band, wherein checking integrity of the tamper-evident band comprises transporting a container to a measurement and control position, illuminating the tamper-evident band, and, using an optoelectronic sensor system, detecting an image of at least a sub-region of the tamper-evident band, wherein illuminating the tamper-evident band comprises illuminating the tamper-evident band from inside the container, and wherein illuminating the tamper-evident band from inside the container comprises directing an illumination beam that originates at a light source exterior to the container through a container wall of the container and into an interior of the container at a region of a container seal.

Practices of the invention include those in which detecting an image of at least a sub-region of the tamper-evident band includes using at least one optoelectronic sensor in the optoelectronic sensor system, those in which detecting an image of at least a sub-region of the tamper-evident band comprises recording an image of the tamper-evident band in at least a sub-region thereof, and those in which detecting an image of at least a sub-region of the tamper-evident band comprises recording an image of the tamper-evident band using at most a single optoelectronic sensor by deflecting light from a first optical beam deflection element and deflecting light from a second optical beam deflection element.

In some practices, container is made of a translucent material, in which case the method further comprises illuminating a region of the tamper-evident band from inside the container.

In other practices, a region of a container circumferential surface lies opposite the region of the tamper-evident band. In such cases, the method comprises directing a light beam from the light source so as to strike the region, Yet other practices include directing the light beam along a direction that, at least outside the container, forms an angle of less than 90 degrees relative to at least one of a container axis and a container seal, wherein the angle opens toward a container base lying opposite the container seal.

Additional methods include determining beam refraction resulting from passage of the beam through a container wall, and taking the beam refraction into account, directing the beam along a direction selected such that the beam strikes a back surface of the band directly.

Yet other embodiments, include determining beam refraction on the container wall and/or on the border surface between the container wall and the filler, and, taking the beam refraction into account, directing the beam along a direction selected such that the beam strikes a back surface of the band indirectly as a result of reflection from an inner surface of the container.

Yet other practices include directing an illumination beam comprises directing the beam toward a base of the container.

Practices of the invention also include generating a signal indicative of detecting a container having a defective tamper-evident band, and, in response to the signal, rejecting the container.

Also among the practices of the invention are those in which the tamper-evident band is provided on a sealing body, those in which it is provided on a cap, and those in which the containers are bottles.

In another aspect, the invention features an apparatus for processing containers Such an apparatus includes a device for checking integrity of tamper-evident bands provided on container seals that are used to seal filled containers in either a form-locking manner or a force-locking manner, and in which opening the container is only possible by either removing or destroying the tamper-evident band. The integrity-checking device has a measurement and control position, a transporter, a light source, and an optoelectronic sensor system. The transporter is configured for transporting a container to the measurement and control position. The light source, which is disposed outside the container, emits an illumination beam that illuminates the tamper-evident band by directing it through a container wall and into an interior of the container to a region of the container seal, thereby illuminating the tamper-evident band from the interior of the container. The optoelectronic sensor system then detects an image of at least a sub-region of the tamper-evident band.

In some embodiments, the optoelectronic sensor system is configured for detecting numerous sub-regions of the tamper-evident band.

In other embodiments, the optoelectronic sensor system includes a shared optoelectronic sensor and an optical system. In these embodiments, the optical system comprises beam deflection elements that cooperate with the shared optoelectronic sensor to simultaneously record numerous sub-regions of the tamper-evident band.

In yet other embodiments, the optical system has a first optical deflection element, a second optical deflection element, and a third optical deflection element.

The first optical beam deflection element is displaced laterally from the measurement and control position. The second optical beam deflection element adjoins the first optical beam deflection element along a beam path of the illumination beam. The first and second beam deflection elements are distributed about the measurement and control position. The third optical beam deflection element is provided in the beam path between the second beam deflection element and the optoelectronic sensor. The third beam deflection element is disposed to intersect an optical axis of the optoelectronic sensor, which is also an axis of the measurement and control position.

Among these embodiments are those in which the container has a container base and a container seal disposed opposite the container seal. In such embodiments, the light source is disposed beneath the first optical deflection element. A beam incident on the first optical deflection element lies in a plane containing the optical axis and forms an angle with the optical axis that is less than 90° and that opens toward a plane defined by the container base.

Other embodiments include a housing, and a supporting structure for the housing, the supporting structure has a base pillar. At least one of the first beam deflection element and the light source is contained in the base pillar, which is disposed to a side of a movement path of the container. The housing, which accommodates the sensor is disposed above the movement path for the container.

In some embodiments, the illumination beam is a bundled light beam for illuminating the tamper-evident band, and wherein the bundled light beam is to be detected by the optoelectronic sensor system. Among these are embodiments in which the illumination beam is directed so as to illuminate the tamper-evident band from inside the container when the container is a translucent container that is located at the measurement and control position.

In another embodiment, the device for checking integrity of tamper-evident bands is a constituent of a container-processing machine. The container-processing machine can be, but is not limited to a container-filling machine, a container-sealing machine, a container-labeling machine, and a container-packaging machine. In these embodiments the device is disposed in the system along a direction of transport for containers to be processed by the container-processing machine.

Refinements, advantages and potential applications of the invention can also be derived from the following description of embodiments and from the figures. At the same time, all of the features described and/or illustrated are, per se, or in any combination, in principle the subject matter of the invention, regardless of their summary in the claims or back references thereto. The content of the claims is also made an integral part of the description.

DESCRIPTION OF THE FIGURES

The invention will next be explained in more detail with the aid of the figures, on the basis of one embodiment. In the figures.

DETAILED DESCRIPTION

Figure 1:
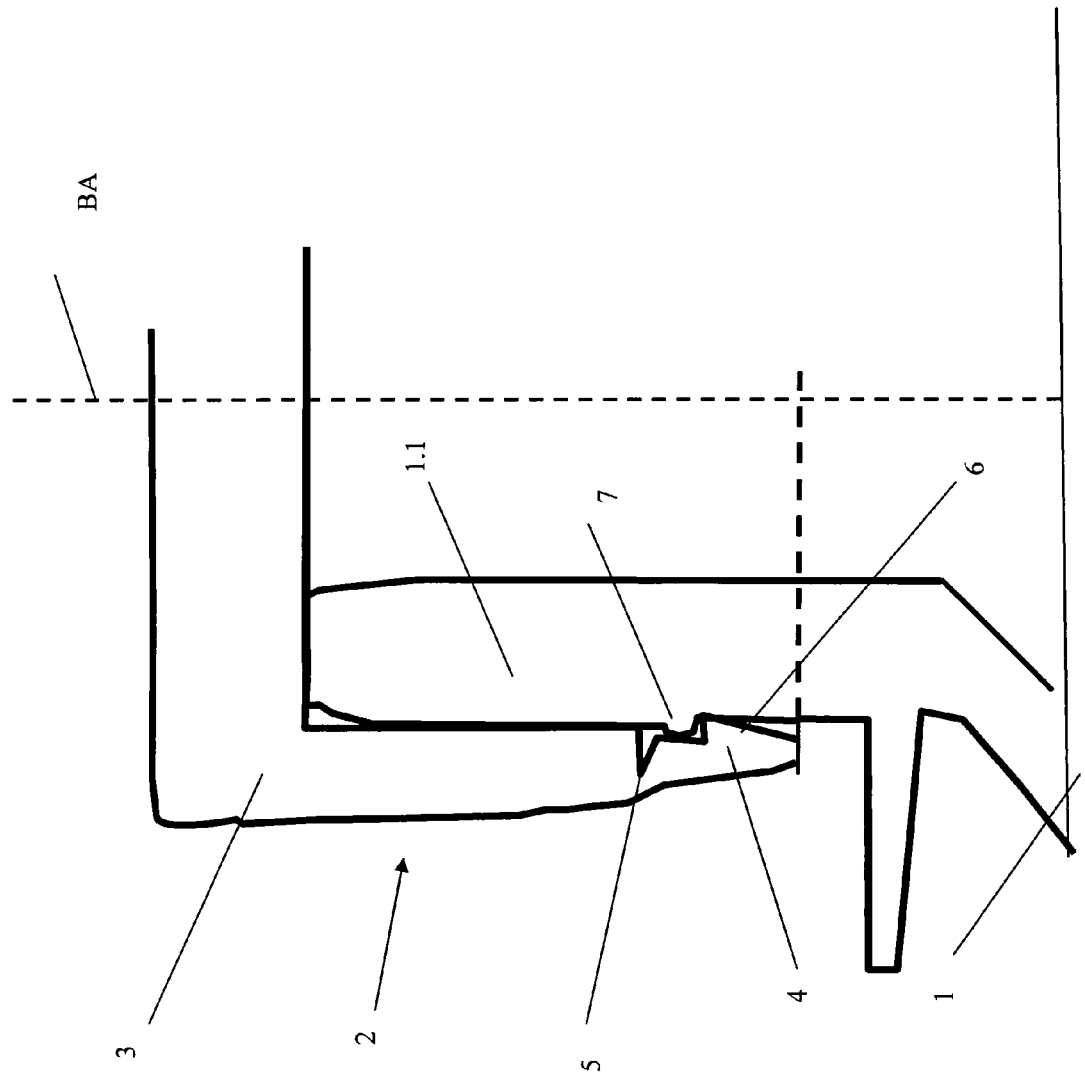
FIG. 1 is a simplified partial diagram form and in section, a container closure with an originality-security ring arranged on a mouth of a container or a bottle.

The figures show containers 1, generally bottles, which are preferably made from a light-permeable or translucent material. Examples of such materials include glass and translucent plastics, such as PET. Following filling with a bulk product, for example with a beverage, each container 1 is closed with a cap-type container closure 2, for example by screwing on the container closure 2 or a closure body 3 thereof onto an external thread on a container neck 1.1, as shown in FIG. 1.

Each container closure 2 includes a cap-type closure body 3 and an originality-security ring 4, also referred to as a "tamper-evident band," which is produced integrally with the closure body 3 via a ring-shaped predetermined break-line 5 concentrically surrounding a closure and container axis BA. The break-line 5 is formed by a perforation with several slit-like breaks arranged in sequence along the predetermined break-line 5, and is made, for example, of plastic or a metallic material. The originality-security ring 4 is provided on the inside with several projections or catches 6 that are distributed around the axis of the closure and that engage from behind in a positive fit with a ring-type projection 7 that stands away from the perimeter area of the container mouth 1. As a result, it is only possible to open the container 1 by at least partially separating the originality-security ring 4 along the predetermined break line 5 and/or by at least partially destroying the originality-security ring 4.

The container closures 2 are designed in such a way that their originality-security rings 4 are destroyed, as described above, under the stress that occurs during opening. However, it also occasionally happens that the originality-security ring 4 is damaged during closing, rather than opening the container. For example, it may be damaged while being screwed onto the container neck 1.1.

This can give the consumer the impression that the container has already been opened, even though it has not.

Figure 3:
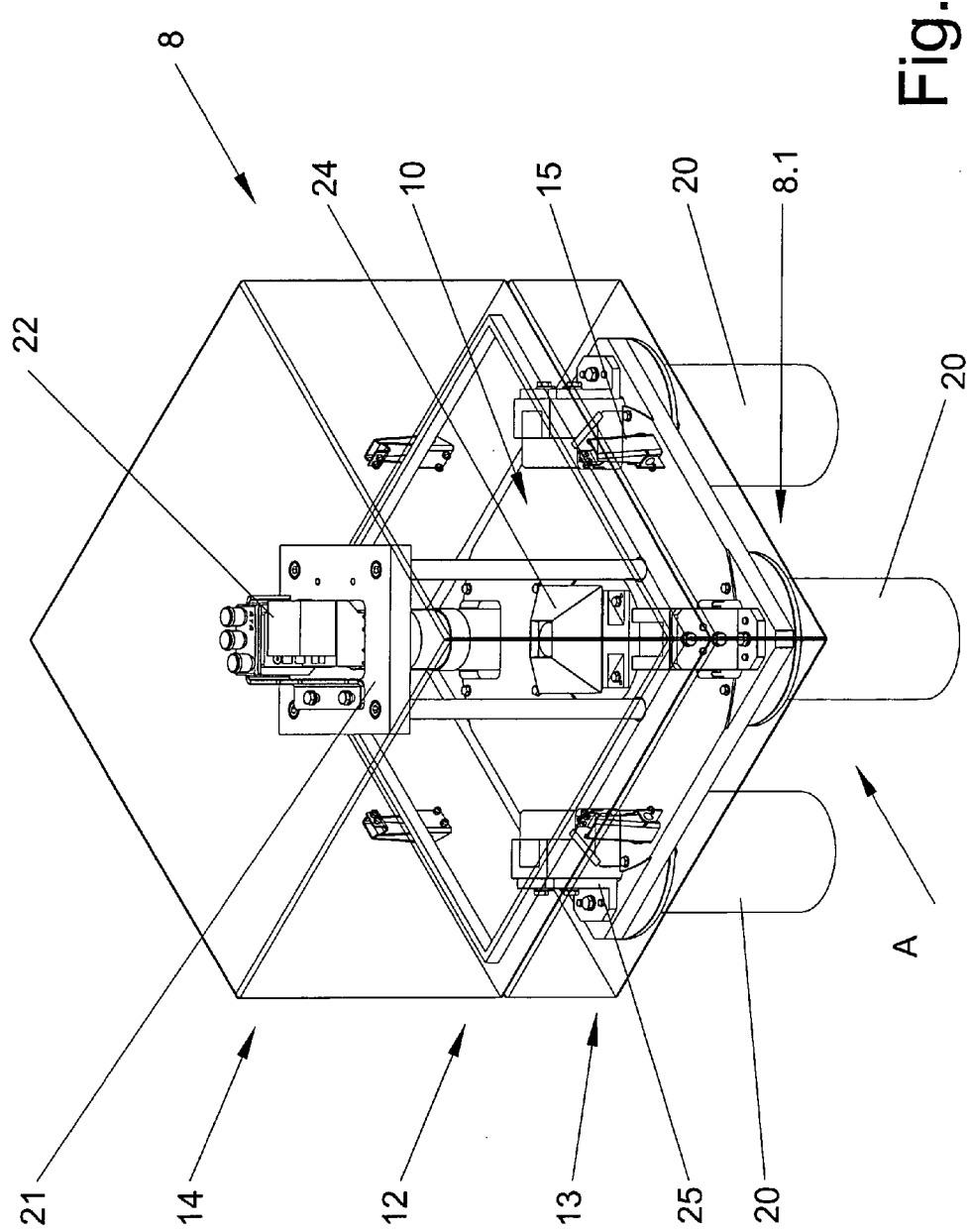
FIG. 3 shows the inspection device from FIG. 2 in perspective view.

FIG. 3 shows an inspection device 8 for checking the intactness of the originality-security rings 4 on the container closures after a container 1 has been filled and closed. Preferably, this inspection takes place before each closed container 1 is passed on for further processing. Examples of machines used for further processing include a labeling machine, a machine for placing the containers 1 in transport crates (bottle crates), and a machine that forms multipacks of several containers. Consequently, it is especially advantageous if the check of the intactness of the originality-security rings 4 takes place prior to delivery or shipping of the filled and sealed containers 1 to customers, for example to drink outlets, etc.

Figure 2:
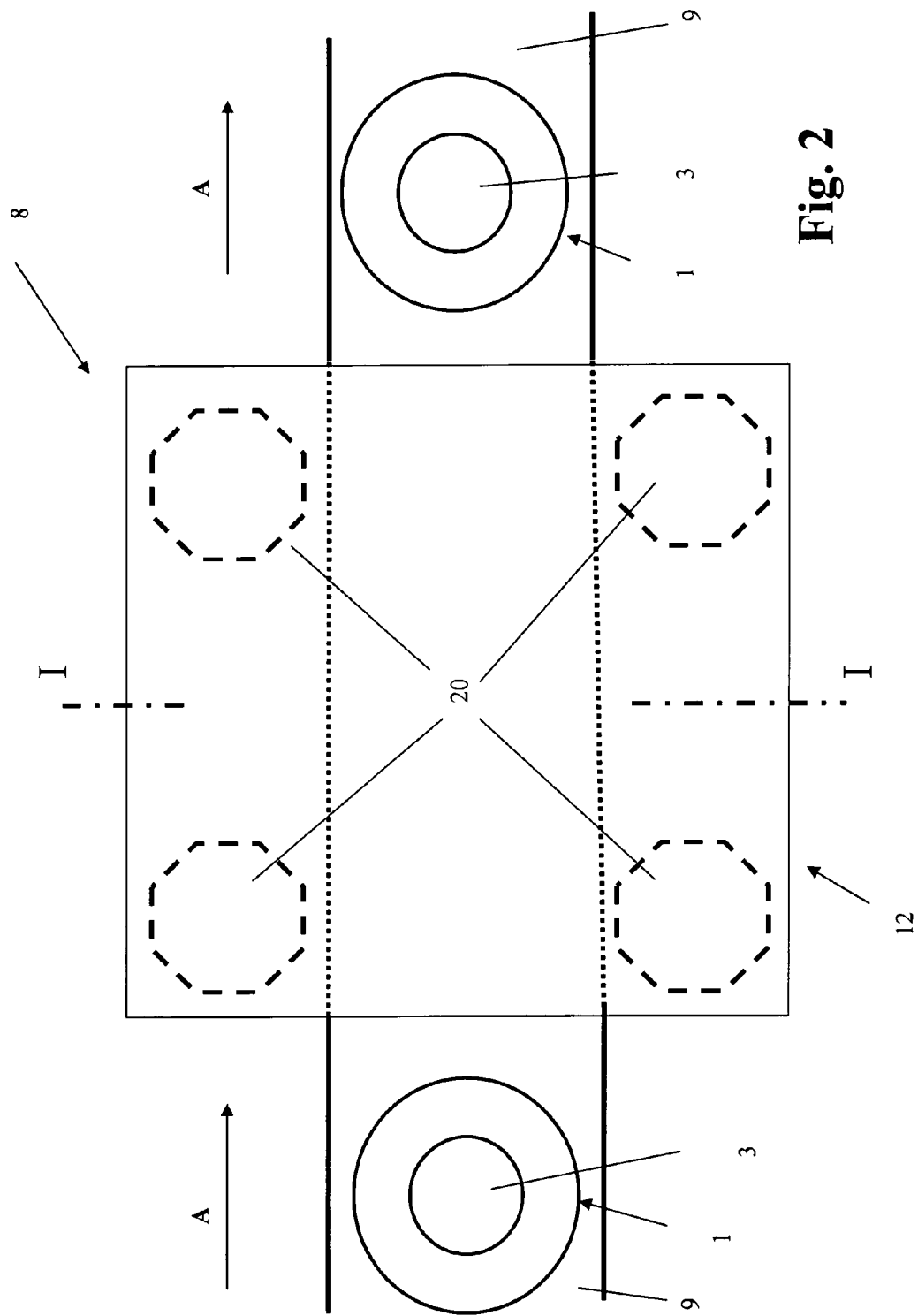
FIG. 2 is a top view of an inspection device according to the invention for testing the originality-security rings of closed containers.

Referring to FIG. 2, to carry out the inspection, the containers 1, which are, for example, standing upright on a conveyor 9, i.e. with their container axis BA vertically oriented, are moved continuously or in pulses in a transport direction A through the inspection device 8 and thereby also through a measurement and control position 8.1 of the inspection device 8. At the measurement and control position 8.1, an optoelectronic sensor system 10 captures image data concerning the originality-security ring 4. The optoelectronic sensor system 10 delivers this data for processing by an image-processing system 11. The image processing system 11 comprises or is aided by a computer.

Processing by the image-processing system 11 includes evaluating the actual data delivered by the sensor system 10 on each checked originality-security ring 4. For example, the actual data delivered on each checked originality-security ring 4 is compared with target data or values stored in a memory of the image processing system 11. If a fault is found on an originality-security ring 4, the image processing system 11 takes appropriate action. In one example, the image-processing system 11 triggers a fault signal, which then leads e.g. to the container 1 with the closure with the faulty originality-security ring 4 being expelled from a product line of a plant that is using the inspection device 8.

Referring to FIG. 3, the inspection device 8, in the illustrated embodiment, has a two-part housing 12 in which the sensor system 10 is housed and that essentially consists of a solid housing lower part 13 and a housing upper part 14. The housing upper part 14 is detachably fixed to the housing lower part 13 via toggle fasteners 15. The housing lower part 13 is relatively solid by design. In the embodiment shown, the housing lower part 13 is in the form of a trough, with a square base 16 and a perimeter wall 17. The housing upper part 14 closes off the housing part 13 on the open upper side is designed in the form of a hood, with a square upper wall 18 and a perimeter wall 19, best seen in FIG. 4.

The housing 12, which is thus square in top view, is arranged with four feet 20, each of which is a hollow cylinder. The housing underside, formed by the square base 16, lies above the movement path of the containers 1 moved through the inspection device 8. The feet 20 are located to the side of the conveyor 9 near the corners of the square base 16. Also, the arrangement is made in such a way that two sides of the housing 12 are oriented parallel to the transport direction A of the conveyor 9 and two sides of the housing 12 are oriented perpendicular to the transport direction A.

Figure 4:
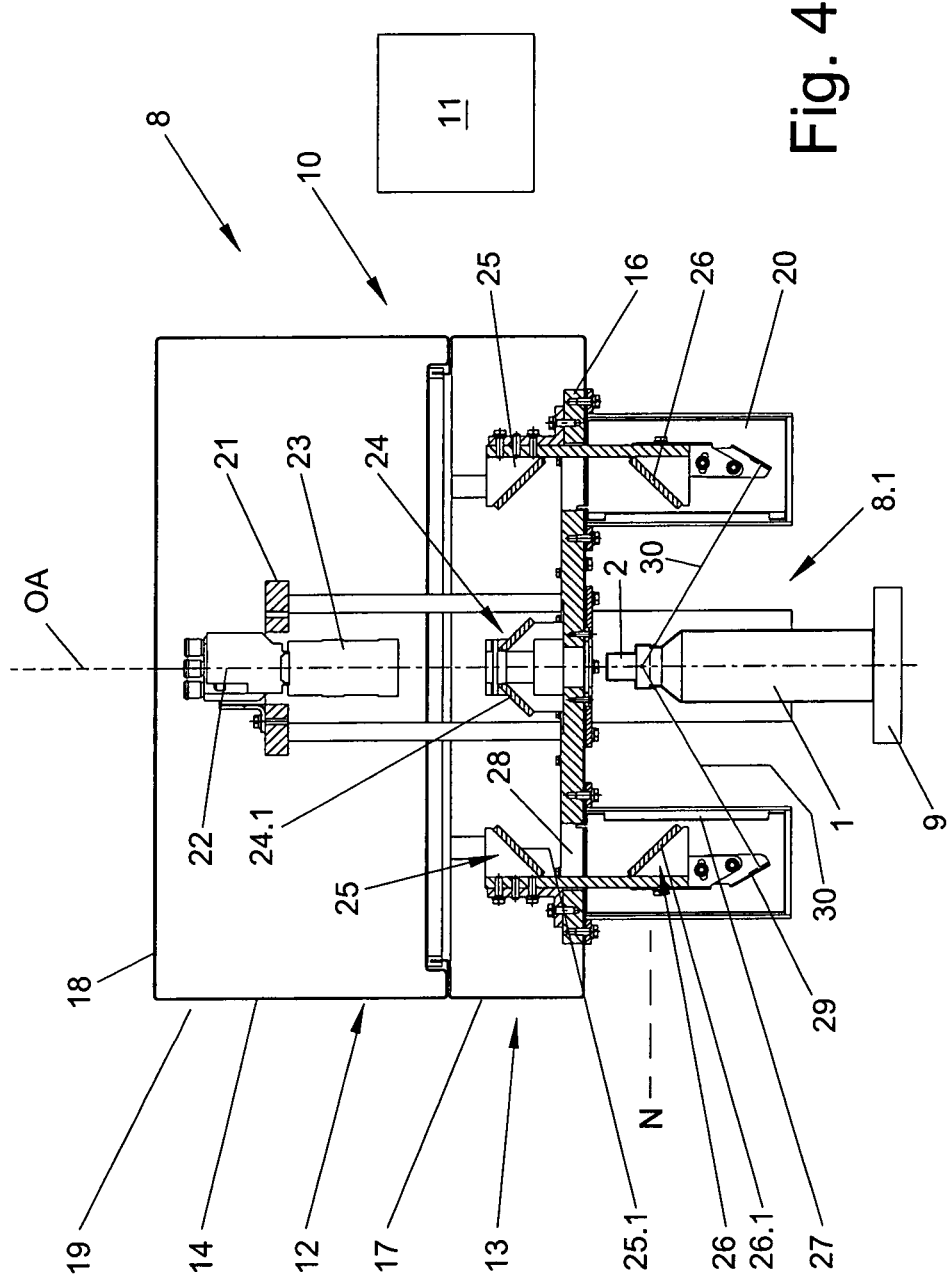
FIG. 4 is a section along the line I-I in FIG. 2.

Referring now to FIG. 4, an electronic camera 22 with a lens system 23, which is directed at the housing base 16, is arranged on a supporting frame 21 in the interior of the housing 12. This is done in such a way that the camera 22 and the lens system 23 have a vertically oriented with common optical axis OA. The optical axis OA defines both an axis of symmetry of the sensor system 10 and an axis of the measurement and control position 8.1 in the form that each container 1 which has reached this measurement and control position 8.1, is arranged with its container axis BA coaxial, or essentially coaxial with the axis OA.

In the embodiment shown, the point at which the diagonals of the square housing base 16 intersect and the point at which the connecting lines between the axes of the feet 20 that lie diagonally opposite each other in relation to the square housing base 16 intersect both lie on the optical axis OA.

A multi-mirror optical beam deflection element 24 is provided underneath the camera 22 and separated from it by a distance from it in the vertical direction. The multi-mirror optical beam deflection element 24 has a mirror body shaped like a pyramid having a square base. Four mirror surfaces 24.1 are on the mirror body.

The multi-mirror optical beam deflection element 24 is arranged with its axis in the optical axis OA so that each mirror surface 24.1 of a beam deflection element 24 lies opposite and at a distance from a first mirror surface 25.1 of a mirror 25 that is arranged inside the housing 12 and above the foot 20 in which the beam deflection element 24 is disposed. The first mirror surface 25.1 lies opposite a second mirror surface 26.1 of a mirror 26 that is arranged in a foot element 20 behind a window 27 provided in the foot element 20 and sealed off by a transparent protective pane made from a transparent material, for example glass. An opening 28 in the base 16 between the beam deflection elements 25 and the mirror 26 allows optical communication therebetween.

The mirror 26 and its mirror surface 26.1 are located at a height level N at which the originality security rings 4 on the containers 1 to be checked are moved through the measurement and control position 8.1. Via the mirror surfaces 24.1, 25.1 and 26.1, the beams imaging the originality security ring 4 at the measurement and control position 8.1 are each subjected to multiple deflection by 90°. This results in a ray path that starts from the measurement and control position 8.1, radially outwards in relation to the optical axis OA, proceeds subsequently by deflection at the mirror surface 26.1 parallel to the optical axis OA upwards through the opening 28 at the mirror surface 25.1, from this, in relation to the optical axis OA, radially inwards to one of the mirror surfaces 24.1, where it is deflected into the lens system 23 of the camera 22.

Due to the arrangement of the mirrors 26, an image is captured of the originality security ring 4 from the side. With corresponding design of the sensor system 10 or with corresponding arrangement of the mirrors 26, it is also possible to capture an image of the originality-security rings 4 from another viewing direction, for example at an angle from above or at an angle from below.

A light source 29 is disposed in the foot element 20, under the mirror 26, and behind the window 27. As a result, the light source 29 is likewise protected against contamination. This light source 29 emits an intensely focused illumination light beam 30 directed upwards at an angle starting from the light source 29 towards a point at which it intersects the optical axis OA. The light beam 30 illuminates the container closure 2, at least on the area with the originality-security ring 4 on the inside of the container closure, and in fact through the container 1, and in certain cases, depending on the application, also through the bulk product contained in the container 1, thus from the inside of the container 1. As a result, wherein from the outside of the container, the container closure 2, and thus, in particular, the originality-security ring 4, appears to be lit from behind. In order to achieve this, the light beam 30 preferably impinges in a direction on the side of the originality-security ring 4 facing towards the interior of the container. This direction is coaxial with the optical axis of the mirror 26 of the respective mirror system formed by the mirrors 25 and 26, or else encloses an angle considerably smaller than 90° with this optical axis.

The mirror arrangement formed by the mirrors 25 and 26 is provided four-fold, i.e. a mirror 25 is arranged over each foot element 20 and the opening 28 provided there, to which a mirror 26 is assigned in the foot element 20. Furthermore, in each foot element 20 a light source 29 is provided to emit the intensely bundled light beam 30, and in such a way that the container closure 2 of the respective container 1 located at the measurement and control position 8.1 is lit from behind by the light source 29 in the area of its originality-security ring 4 for imaging via one respective mirror 26, the light source being provided in the foot element 20 located diagonally opposite this mirror 26.

By pivoting the light source 29, the beams 30 can be adjusted in such a way that the refraction that these light beams 30 undergo when entering the respective container 1 at its surface or perimeter area and the refraction arising from the interface between the container wall and the liquid bulk product, can be taken into account for an optimal illumination of the originality-security rings 4 from behind.

Due to the illumination of the originality-security rings 4 from behind, i.e. from the inside of the respective containers 1, the backlight thus generated gives rise to an especially contrast-rich 360° image of the respective originality-security ring 4 captured with the camera 22 via the mirrors 24, 25 and 26. This contrast-rich image makes it possible for the image processor 11 to reliably identify any faults or damage on originality-security rings 4. The illumination of the respective originality-security ring 4 from behind also leads to especially contrast-rich and clear images because the container closures 2 usually consist of a material that is non-translucent or the translucency of which is considerably less than that of the material from which the containers 1 are made.

The invention has been described above on the basis of one embodiment. It goes without saying that numerous modifications and alterations are possible.

For example, it has been assumed above that the intensely bundled light beams 30 are generated by light sources 29 that are arranged at the side of the container located respectively at the measurement and control position 8.1, and in such a way that the light beams 30 strike the respective container 1 or its perimeter wall at an angle from below, and in fact in the upper area of the container 1, e.g. in the area of the container shoulder or container breast. In principle, embodiments are also possible in which the originality-security ring 4 to be checked is illuminated from behind through the container base.

It is also possible to provide several light sources 29 to illuminate that area of the originality-security ring 4 that is to be captured with the camera 22 or with another optoelectronic sensor unit.

It has also been assumed above that the optoelectronic system for capturing the condition of the respective originality-security ring 4 is a camera system with an electronic camera 22. However, this system may also have several electronic cameras or consist of a system with which the respective originality-security ring 4 and its condition are optically captured in some other way, for example by scanning with at least one laser beam, etc.

The optical beam deflection elements to achieve a 360° capture or 360° image of an originality-security ring 4 have been described above as mirrors 24, 25 and 26. However, other optical beam deflection elements can also be used.

Having described the invention, and a preferred embodiment thereof, what we claim as new and secured by Letters Patent is:

1. A method for checking filled containers that have been sealed with container seals, said method comprising checking integrity of a tamper-evident band provided on a container seal that is retained on a container in at least one of a form locking manner and a force locking manner when said container is sealed, wherein said container can only be opened by at least one of removal and destruction of said tamper-evident band, wherein checking integrity of said tamper-evident band comprises transporting a container to a measurement and control position, illuminating said tamper-evident band, and, using an optoelectronic sensor system, detecting an image of at least a sub-region of said tamper-evident band, wherein illuminating said tamper-evident band comprises illuminating said tamper-evident band from inside said container, and wherein illuminating said tamper-evident band from inside said container comprises directing an illumination beam that originates at a light source exterior to said container through a container wall of said container and into an interior of said container at a region of a container seal.

2. The method of claim 1, wherein detecting an image of at least a sub-region of said tamper-evident band comprises using at least one optoelectronic sensor in said optoelectronic sensor system.

3. The method of claim 1, wherein detecting an image of at least a sub-region of said tamper-evident band comprises recording an image of said tamper-evident band in at least a sub-region thereof.

4. The method of claim 1, wherein detecting an image of at least a sub-region of said tamper-evident band comprises recording an image of said tamper-evident band using at most a single optoelectronic sensor by deflecting light from a first optical beam deflection element and deflecting light from a second optical beam deflection element.

5. The method of claim 1, wherein said container is made of a translucent material, and wherein said method further comprises illuminating a region of said tamper-evident band from inside said container.

6. The method of claim 5, wherein a region of a container circumferential surface lies opposite said region of said tamper-evident band, and wherein said method comprises directing a light beam from said light source so as to strike said region.

7. The method of claim 5, further comprising directing said light beam along a direction that, at least outside said container, forms an angle of less than 90 degrees relative to at least one of a container axis and a container seal, wherein said angle opens toward a container base lying opposite said container seal.

8. The method of claim 5, further comprising determining beam refraction resulting from passage of said beam through a container wall, and taking said beam refraction into account, directing said beam along a direction selected such that said beam strikes a back surface of said band directly.

9. The method of claim 5, further comprising determining beam refraction on said container wall and/or on said border surface between said container wall and said filler, and, taking said beam refraction into account, directing said beam along a direction selected such that said beam strikes a back surface of said band indirectly as a result of reflection from an inner surface of said container.

10. The method of claim 1, wherein comprising directing an illumination beam comprises directing said beam toward a base of said container.

11. The method of claim 1, further comprising generating a signal indicative of detecting a container having a defective tamper-evident band, and, in response to said signal, rejecting said container.

12. The method of claim 1, wherein said tamper-evident band is provided on a sealing body.

13. The method of claim 1, wherein said tamper-evident band is provided on a cap.

14. The method of claim 1, wherein said containers are bottles.

15. An apparatus for processing containers, said apparatus comprising a device for checking integrity of tamper-evident bands provided on container seals used to seal filled containers in at least one of a form locking manner and a force locking manner, wherein opening said container is only possible by at least one of removal and destruction of said tamper-evident band, wherein said device for checking integrity of said tamper-evident bands comprises a measurement and control position, a transporter, a light source, and an optoelectronic sensor system, wherein said transporter is configured for transporting a container to said measurement and control position, wherein said light source is disposed outside said container, wherein said light source emits an illumination beam, wherein said light source is configured for illuminating said tamper-evident band with said illumination beam, wherein said light source is configured to direct said illumination beam through a container wall of said container, into an interior of said container in a region of said container seal, thereby illuminating said tamper-evident band from said interior of said container, and wherein said optoelectronic sensor system is configured for detecting an image of at least a sub-region of said tamper-evident band.

16. The apparatus of claim 15, wherein said optoelectronic sensor system is configured for detecting numerous sub-regions of said tamper-evident band.

17. The apparatus of claim 15, wherein said optoelectronic sensor system comprises a shared optoelectronic sensor and an optical system, wherein said optical system comprises beam deflection elements, and wherein said shared optoelectronic sensor and said beam deflection elements are configured such that numerous sub-regions of said tamper-evident band can simultaneously be recorded.

18. The apparatus of claim 17, wherein said optical system comprises a first optical deflection element, a second optical deflection element, and a third optical deflection element, wherein said first optical beam deflection element is displaced laterally from said measurement and control position, wherein said second optical beam deflection element adjoins said first optical beam deflection element along a beam path of said illumination beam, wherein said first and second beam deflection elements are distributed about said measurement and control position, wherein said third optical beam deflection element is provided in said beam path between said second beam deflection element and said optoelectronic sensor, wherein said third beam deflection element is disposed to intersect an optical axis of said optoelectronic sensor, and wherein said optical axis of said optoelectronic sensor is an axis of said measurement and control position.

19. The apparatus of claim 15, wherein said illumination beam is a bundled light beam for illuminating said tamper-evident band, and wherein said bundled light beam is to be detected by said optoelectronic sensor system.

20. The apparatus of claim 19, wherein said illumination beam is directed so as to illuminate said tamper-evident band from inside said container when said container is a translucent container that is located at said measurement and control position.

21. The apparatus of claim 18, wherein said container has a container base and a container seal, wherein said container base is disposed opposite said container seal, wherein said light source is disposed beneath said first optical deflection element, wherein a beam incident on said first optical deflection element lies in a plane containing said optical axis and forms an angle with said optical axis that is less than 90°, and wherein said angle opens toward a plane defined by said container base.

22. The apparatus of claim 18, further comprising a housing, and a supporting structure for said housing, said supporting structure comprising a base pillar, wherein at least one of said first beam deflection element and said light source is contained in said base pillar, wherein said base pillar is disposed to a side of a movement path of said container, wherein said housing is disposed above said movement path for said container, and wherein said housing accommodates said optoelectronic sensor.

23. The apparatus of claim 15, wherein said device for checking integrity of tamper-evident bands is a constituent of a container-processing machine selected from the group consisting of a container-filling machine, a container-sealing machine, a container-labeling machine, and a container-packaging machine, wherein said device is disposed in said system along a direction of transport for containers to be processed by said container-processing machine.

* * * * *